United States Patent [19]

Filley et al.

[11] Patent Number: 4,548,817

[45] Date of Patent: Oct. 22, 1985

[54] COMPOSITION AND METHOD FOR TREATING MAMMALIAN ACIDOSIS

[75] Inventors: Giles F. Filley, Denver; Neal B. Kindig, Boulder, both of Colo.

[73] Assignee: Webb-Waring Lung Institute, Denver, Colo.

[21] Appl. No.: 572,235

[22] Filed: Jan. 20, 1984

[51] Int. Cl.$^4$ .............................................. A67K 33/00
[52] U.S. Cl. .................................................... 424/127
[58] Field of Search ........................................ 424/127

[56] References Cited

PUBLICATIONS

*Chemical Abstracts,* vol. 56 12249b; vol. 70 (1969) 104490w.

*Primary Examiner*—Frederick E. Waddell
*Attorney, Agent, or Firm*—Edwin L. Spangler, Jr.

[57] ABSTRACT

This invention relates to an improved parenteral composition for the treatment of acidosis in mammals which comprises a mixture of sodium carbonate and sodium bicarbonate with a pharmaceutically acceptable diluent. The invention also encompasses the method of treating the acidotic condition which comprises the parenteral administration of the composition described above.

9 Claims, No Drawings

COMPOSITION AND METHOD FOR TREATING MAMMALIAN ACIDOSIS

In diabetes, trauma and many renal diseases, acid products accumulate in the body creating a condition known as metabolic acidosis. For some sixty years, an aqueous solution of sodium bicarbonate in concentrations ranging from 0.2 to 1.0 molar has been the prevailing intravenous treatment for this condition provided the patient was breathing or otherwise adequately ventilated which was usually the case. Sodium bicarbonate usually proved to be an effective and relatively safe drug for lowering the hydrogen ion concentrate and it still is, if and only if, once again, the patient is breathing normally or the lungs are being otherwise ventilated. When administered intravenously, its action in the body is in accordance with the well known reaction:

$$HCO_3^- + H^+ \rightarrow H_2O + CO_2 \uparrow \quad (i)$$

where the hydrogen ion concentration is lowered and the pH of the patient elevates to the desired level upon exhalation. It is essential, however, for the carbon dioxide to be removed for the equilibrium to shift to the right and correct the acidic condition.

In more recent times, specifically, the last thirty years or so, traditional sodium bicarbonate solutions are being administered in a manner that has proven to have dangerous and sometimes even fatal consequences. The reasons for this are numerous, complex and, all too often, not well understood. The main problem is the widespread use of concentrated sodium bicarbonate under emergency conditions when ventilation, circulation or both are impaired as in patients in cardiopulmonary arrest. These solutions are being injected in such patients more rapidly and in much higher total dosage than ever before. This is because it is frequently forgotten that without adequate ventilation a significant rise of blood pH does not result from NaHCO3 injections. Thus, the patient may be reinjected repeatedly in a futile attempt to bring the pH to near normal (7.4). Sometime later, when ventilation is restored, blood pH rises to alkalotic levels, 7.5 or higher, showing that the patient was overdosed, perhaps fatally, since reversing severe alkalosis is extremely difficult to achieve.

The conditions under which such emergency treatment is given to the patient explain, at least in part, why this occurs. To begin with, a physician trained in emergency procedures is often not present. All too often, the emergency is being attended to in the ambulance on the way to the hospital by relatively unskilled personnel. Even with physicians present, too few of them realize the high CO2 tension in the traditional solutions and their danger, especially to a non-breathing or poorly ventilated patient. In those instances where the personnel are trained and instructed to only administer these massive doses of bicarbonate to a patient who is breathing or being breathed, the logistics of the emergency can still sometimes result in an overdosed patient simply because the person responsible for giving the injection gets his or her job done before others get an airway established, the lungs ventilated, and the circulation restored.

The whole situation is further complicated by the fact that other serious side effects often occur as a result of rapid intravenous administration of sodium bicarbonate in concentrated form even to a breathing patient. These other side effects have been recognized for some time and form the subject matter of a few papers on the subject, specifically: Bishop, R. L. and Weisfeldt, M. L. Sodium bicarbonate administration during cardiac arrest. JAMA 235,506–509, 1976; and, Bureau, M. A., Begin, R., Berthiaume, Y., Shapcott, D., Khoury, K., and Gagnon, N. Cerebral Hypoxia from bicarbonate infusion in diabetic acidosis. J. Pediatrics 96,968–973, 1980. The first publication by the inventors on the improved acute acidosis therapy forming the subject matter hereof appeared in a letter to the editor referenced as follows: Kindig, N. B. and Filley, G. F. Intravenous bicarbonate may cause transient intracellular acidosis. Chest 83,712, 1983. While the chemistry and physiology is complex and even now not fully understood, these side effects are considered to stem (a) from the abnormally high CO2 tension both existing in and generated by the solution which results in the CO2 diffusing into the heart and brain cells (thereby causing intracellular acidosis as protons are produced inside the cells thus lowering their pH) and, (b) from the high osmolarity of the solution bringing about a rise in plasma osmolarity and its circulatory consequences, the latter forming the subject of the following: Mattar, J. A., Weil, M. H., Shubin, H. and Stein, L. Cardiac arrest in the critically ill II Hyperosmolal states following cardiac arrest. Am. J. Med. 56,162–168, 1974.

Traditional one molar NaHCO3 solution has a PaCO2 well over 200 mm Hg and this, plus the generation of CO2 by reaction (i) cited above, raises the physically dissolved CO2 in the blood in addition to raising the concentration of HCO3−. Because the PaCO2 in the blood is raised above that in the body cells, CO2 diffuses into the cells but the HCO3− diffuses in much less rapidly. The result, as seen by equation (ii) below, is that intracellular pH falls. In ventilated patients this fall is transient, but in cardiac arrest, when heart muscle cell acidosis must be combatted, this transient pH fall, with its negative inotropic effect, is an unwanted side consequence of bicarbonate therapy. The similar known and measured "paradoxical" CSF acidosis following NaHCO3 therapy is generally agreed to be caused by dissolved CO2 released when HCO3− accepts blood protons (see Posner, J. B. and Plum, F. Spinal fluid pH and neurologic symptoms in systemic acidosis. New England J. Med 227,605–613, 1967.)

The traditional NaHCO3 solution has an osmolarity of 2000 mOsm/L so that repeated doses raise blood osmolarity considerably. This increases the plasma volume and in patients with inadequate circulation can lead to the complications of fluid overload as noted in the Mattar et al paper referred to above.

The prior art related to acidosis therapy has revealed U.S. Pat. Nos. 3,253,988; 3,621,094; and, 4,163,777. These patents disclose antacid compositions wherein the antacid employed is selected from sodium carbonate, sodium bicarbonate and mixtures of the two; however, these compositions are for oral, not intravenous, administration and, therefore, could not be used in emergencies where the patient is incapable of taking medication by mouth. Moreover, even if the patient could ingest these preparations orally, they would be ineffective to bring about the necessary rise in blood pH called for under conditions of acute acidosis demanding emergency measures. The chemistry and physiology involved in intravenous vs. oral administration of even the same drug are altogether different, especially in a situation such as this where injection of a bicarbonate solution into a non-breathing acidotic patient can even cause the pH to drop further as the intended buffering effect is negated and the accumulated $CO_2$ drives the disassociation reaction back to the left.

It has now been found in accordance with the teaching of the instant invention that the above-described harmful side effects resulting from emergency intravenous administration of concentrated sodium bicarbonate solutions can all but be eliminated by the simple, but unobvious expedient of raising the pH of the solution through the use of the carbonate ion as a buffer to control the hydrogen ion concentration. The result is that the $PaCO_2$ is reduced markedly in the solution and even in a patient that is not breathing or is otherwise inadequately ventilated, all without damage to the veins one would expect to result from such a highly alkaline mixture.

Using the Henderson-Hasselbach equation:

$$pH = pKa_1 + \log \frac{[HCO_3^-]}{K_H \times PaCO_2} \quad \text{(ii)}$$

where $pKa_1$ is 6.1 at this ionic strength and the solubility of $CO_2$ (Henry's Law constant) $K_H$ is approximately 0.03 measured in mM/mmHg at body temperature of 37° C., it can be shown that for normal blood the pH is 7.4 with $PaCO_2$ taken at 40 mmHg and the concentration of $HCO_3^-$ at 24 mM. In emergency bicarbonate therapy, on the other hand, a 1 Molar solution has a pH of 8.0 and the $HCO_3^-$ concentration, of course, is 1000 mM. Placing these values in the above equation and solving for $PaCO_2$, we find:

$$8.0 = 6.1 + \log \frac{1000}{.03 \times PaCO_2}$$

$$8.0 = 6.1 + 3 - \log .03 - \log PaCO_2$$

$$\log PaCO_2 = 9.1 - (-1.5) - 8.0 = 2.6$$

$$PaCO_2 = 10^{2.6} = 398$$

The $PaCO_2$, therefore, has a calculated value of about 400. The measured value, in a blood gas machine, is about 200. These machines only measure partial pressures of dissolved blood gases accurately up to 100 mmHg; therefore, based upon the calculated $PaCO_2$ of 400, the statement is made that $PaCO_2 > 200$ mmHg in the inventor's article referenced to previously.

An analysis of the above equation would seem to indicate that the only two ways in which the dangerously high level of $PaCO_2$ can be reduced is to ventilate the patient or raise the pH even higher. As already noted, relying on the patient being adequately ventilated just doesn't work in actual practice and not infrequently, a non-breathing or poorly ventilated patient is overdosed, sometimes to the point of death. On the other hand, increasing the pH of the solution too much is contraindicated because of the very real possibility that venous intimal injury would result. During the World War I era, in fact, highly alkaline carbonate solutions were used inadvertently in acidotic children but then abandoned since $CO_3^{2-}$ in high concentrations is a vein-sclerosing agent, all of which was reported by Howland et al (see Howland, J. and Marriott, WMc. Acidosis occurring with diarrhea. Am. J. Dis. Child. 11, 309–325, 1916.)

The inventors deduced theoretically that the proper mixture of $NaHCO_3$ and $Na_2CO_3$ would eliminate the toxic effects of pure $NaHCO_3$ as currently used. They then found experimentally that a 1:1 mixture raised blood pH without raising blood $PaCO_2$ significantly or damaging veins.

Following some early experiments using venous blood in a closed system, the following experiment was conducted:

Methods. Fifteen, healthy mongrel dogs were anesthetized with 25–40 mg/kg sodium pentobarbital; catheters were placed in a cephalic vein and in a femoral vein and artery. D5 lactated Ringers solution was slowly infused into the cephalic vein cannula. Dogs were ventilated at 20 breaths per minute and tidal volume was adjusted to yield an arterial $CO_2$ tension ($PaCO_2$) of 25–35 mm Hg. Pancuronium was given initially and periodically to insure absence of respiratory effort. End tidal carbon dioxide ($PETCO_2$) was measured on a breath-to-breath basis using a computer controlled mass spectrometer. Hydrochloric acid, 0.2N, (5 meq/kg) was infused into the femoral vein until the bicarbonate (calculated from the Severinghaus slide rule) was less than 11 meq/liter and/or pH was less than 7.1. Within thirty minutes 50 ml of either 1 meq/ml sodium bicarbonate (measured pH 8.3) or a new solution (0.9 meq/ml $Na_2CO_3/NaHCO_3$, pH 9.6, 0.3M $CO_3^{2-}$, 0.3M $HCO_3^-$) were infused over one minute into the cephalic vein. Arterial blood gases were drawn at 0, ½, 1, 1½, 2, 3 and 5 minutes. This sequence was repeated after 10 minutes. The $NaHCO_3$, and the new solution were compared in separate groups of dogs. $PaCO_2$, pH, calculated bicarbonate ($HCO_3^-$) and $PETCO_2$ were recorded prior to each injection and at the given times above. The results for the two groups were compared using an unpaired t-test. In 3 dogs, sections of veins were taken from the area of entry of the new solution, stained and examined by light microscopy.

Results. Seven dogs died during the infusion of HCl. Of the eight surviving dogs, four were given bicarbonate and four were given the new solution. The values of pH, $PETCO_2$, $HCO_3^-$ or $PaCO_2$ peaked at one minute from the start of the alkali injections. Table 1 indicates the relevant results for the two trials in the two groups. $PaCO_2$ and $PETCO_2$ were significantly elevated in the group given $NaHCO_3$ when compared to the group given the new solution at the peak response time of one minute. There was no microscopic evidence of venous intimal injury.

TABLE 1

| | | ONE MINUTE POST: | |
|---|---|---|---|
| | Initial | Injection 1 | Injection 2 |
| Bicarbonate: | ($NaHCO_3$) | (milliosmolarity 2000 mOsm/L) | |
| $PaCO_2$ | 29.8 ± 2.6 | 53.8 ± 5.6* | 49.5 ± 5.7* |
| $PETCO_2$ | 31.8 ± 7.0 | 55.4 ± 4.8* | 50.9 ± 6.9* |
| pH | 7.12 | 7.46 | 7.51 |
| $HCO_3^-$ | 9.0 ± 1.5 | 38.2 ± 14.3 | 39.3 ± 12.4 |
| New Solution: | ($Na_2CO_3/NaHCO_3$) | (1500 mOsm/L) | |
| $PaCO_2$ | 29.6 ± 4.4 | 33.6 ± 4.0* | 30.1 ± 4.1* |
| $PETCO_2$ | 32.2 ± 8.7 | 33.8 ± 5.5* | 33.9 ± 7.4* |
| pH | 7.14 | 7.55 | 7.63 |
| $HCO_3^-$ | 9.8 ± 2.2 | 30.5 ± 9.5 | 32.5 ± 6.1 |

*Significant difference between groups

The mechanism of the usual bicarbonate treatment is that $NaHCO_3$ must be converted to $CO_2$ in order to correct the metabolic acidosis. The instant composition, on the other hand, requires that only very little $CO_2$ be generated to accept the H+ ions and thereby reduce the hydrogen ion concentration because of its higher pH and greater buffering capacity. It can be shown that approximately one liter of $CO_2$ is generated from 50 meq of $NaHCO_3$, whereas, only about 600 cc of $CO_2$ is generated by total acidification of 50 ml of the combined $Na_2CO_3/NaHCO_3$ solution. Finally, as seen in the table, the osmolarity of the new mixture is considerably lower than in $NaHCO_3$ and therefore would contribute less to hyperosmolal states in patients.

Sodium carbonate by itself cannot be safely used in a parenteral solution even though such a solution would solve the carbon dioxide problem, the reason being that the carbonate ion when used as a blood buffer has a pH of around 11 which is known to cause severe vein damage upon direct injection.

What is claimed is:

1. In a method of treating acidosis in a patient who is not breathing or is otherwise inadequately ventilated by an intervenous administration of a solution of sodium bicarbonate, all without damage to the patient's veins the improvement of raising the pH of the sodium bicarbonate solution by adding a solution containing a carbonate ion to the administered sodium bicarbonate solution to form a mixture for administration to the patient in which the hydrogen ion concentration is controlled.

2. The method of treating acidosis as defined in claim 1 in which the solution containing the carbonate ion includes sodium carbonate.

3. The method of treating acidosis as defined in claim 2 wherein the ratio of sodium carbonate to sodium bicarbonate is approximately 1:1.

4. The method of treating acidosis as defined in claim 2 wherein the sodium carbonate has a concentration of between approximately 0.3 and 0.9 Molar and the sodium bicarbonate has a concentration of between approximately 0.3 and 0.9 Molar.

5. The method of treating acidosis as defined in claim 2 wherein the total concentration of both sodium carbonate and sodium bicarbonate does not exceed approximately 1.2 Molar.

6. The method of treating acidosis as defined in claim 2 wherein the sodium carbonate and the sodium bicarbonate concentrations are both approximately 0.3 Molar.

7. In a method of treating acidosis in a patient who is not breathing or is otherwise inadequately ventilated by intervenous administration of a solution of sodium bicarbonate, all without damage to the patient's veins the improvement of adding a solution containing a carbonate ion to the administered sodium bicarbonate solution.

8. The method of treating acidosis as defined in claim 7 wherein the solution containing the carbonate ion includes sodium carbonate.

9. The method of treating acidosis as defined in claim 8 wherein the sodium carbonate has a concentration of between approximately 0.3 and 0.9 Molar and the sodium bicarbonate has a concentration of between approximately 0.3 and 0.9 Molar and further including a pharmaceutically acceptable diluent.

* * * * *